(12) United States Patent
Fukui et al.

(10) Patent No.: US 8,306,605 B2
(45) Date of Patent: Nov. 6, 2012

(54) TOMOGRAPHIC SYSTEM

(75) Inventors: Yasuhiro Fukui, Tsuyama (JP); Toshiyuki Irie, Mito (JP)

(73) Assignee: Hitachi Medical Corporation, Tokyo (JP)

( * ) Notice: Subject to any disclaimer, the term of this patent is extended or adjusted under 35 U.S.C. 154(b) by 715 days.

(21) Appl. No.: 11/632,732

(22) PCT Filed: Jul. 20, 2005

(86) PCT No.: PCT/JP2005/013305
§ 371 (c)(1),
(2), (4) Date: Jan. 17, 2007

(87) PCT Pub. No.: WO2006/009166
PCT Pub. Date: Jan. 26, 2006

(65) Prior Publication Data
US 2008/0030192 A1 Feb. 7, 2008

(30) Foreign Application Priority Data

Jul. 21, 2004 (JP) ................................ 2004-212771

(51) Int. Cl.
*A61B 5/055* (2006.01)
(52) U.S. Cl. ........................................ 600/425; 600/410
(58) Field of Classification Search .................. 382/131; 600/407, 410, 424, 425; 378/4, 20, 21, 146
See application file for complete search history.

(56) References Cited

U.S. PATENT DOCUMENTS

| | | | |
|---|---|---|---|
| 4,998,065 A * | 3/1991 | Koizumi | 324/309 |
| 5,671,157 A * | 9/1997 | Saito | 345/419 |
| 5,740,222 A | 4/1998 | Fujita et al. | |
| 5,748,696 A | 5/1998 | Fujita et al. | |
| 5,848,126 A | 12/1998 | Fujita et al. | |
| 6,032,678 A * | 3/2000 | Rottem | 600/437 |
| 6,160,610 A * | 12/2000 | Toda | 355/41 |
| RE37,356 E * | 9/2001 | Hori et al. | 600/103 |
| 6,341,152 B1 * | 1/2002 | Sugihara | 378/4 |
| 6,424,692 B1 | 7/2002 | Suzuki | |
| 6,725,080 B2 * | 4/2004 | Melkent et al. | 600/424 |
| 6,745,066 B1 * | 6/2004 | Lin et al. | 600/425 |
| 6,894,707 B2 * | 5/2005 | Nemoto | 715/730 |
| 7,458,936 B2 * | 12/2008 | Zhou et al. | 600/437 |
| 2001/0027272 A1 * | 10/2001 | Saito et al. | 600/426 |
| 2002/0103428 A1 | 8/2002 | deCharms | |
| 2003/0007594 A1 | 1/2003 | Ganin | |
| 2005/0228250 A1 | 10/2005 | Bitter et al. | |
| 2006/0078183 A1 | 4/2006 | deCharms | |

FOREIGN PATENT DOCUMENTS

| | | |
|---|---|---|
| JP | 7-148155 | 6/1998 |
| JP | 2000-287962 | 10/2000 |
| JP | 2002-85355 | 3/2002 |
| JP | 2002-219125 | 8/2002 |
| JP | 2004-8398 | 1/2004 |
| WO | WO03/045222 A2 | 6/2003 |

OTHER PUBLICATIONS

Supplementary European Search Report (Nov. 7, 2007) in corresponding European patent application No. EP 05 76 6254.

* cited by examiner

*Primary Examiner* — Tse Chen
*Assistant Examiner* — Rochelle Reardon
(74) *Attorney, Agent, or Firm* — Cooper & Dunham LLP

(57) ABSTRACT

A tomographic system displays plural tomographic images, a relative distance between the tomographic images, whereby the operator can see the displayed data of the relative distances between tomographic images and the length of the treatment device instantaneously, and can therefore determine the insert position or the treatment device for the subject efficiently.

20 Claims, 4 Drawing Sheets

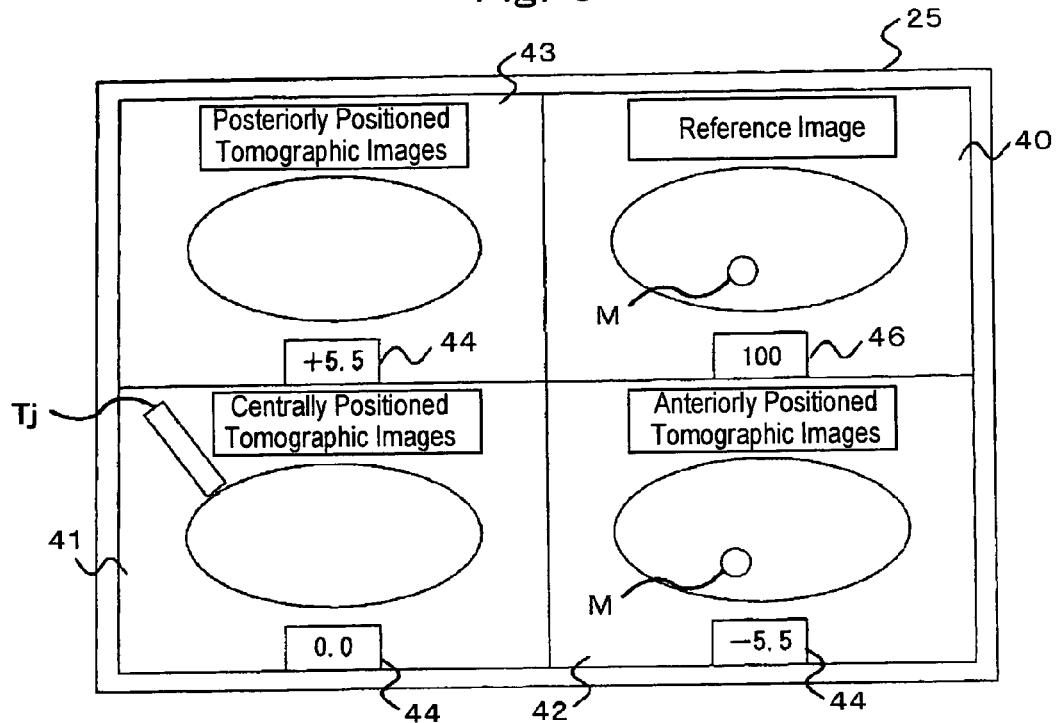
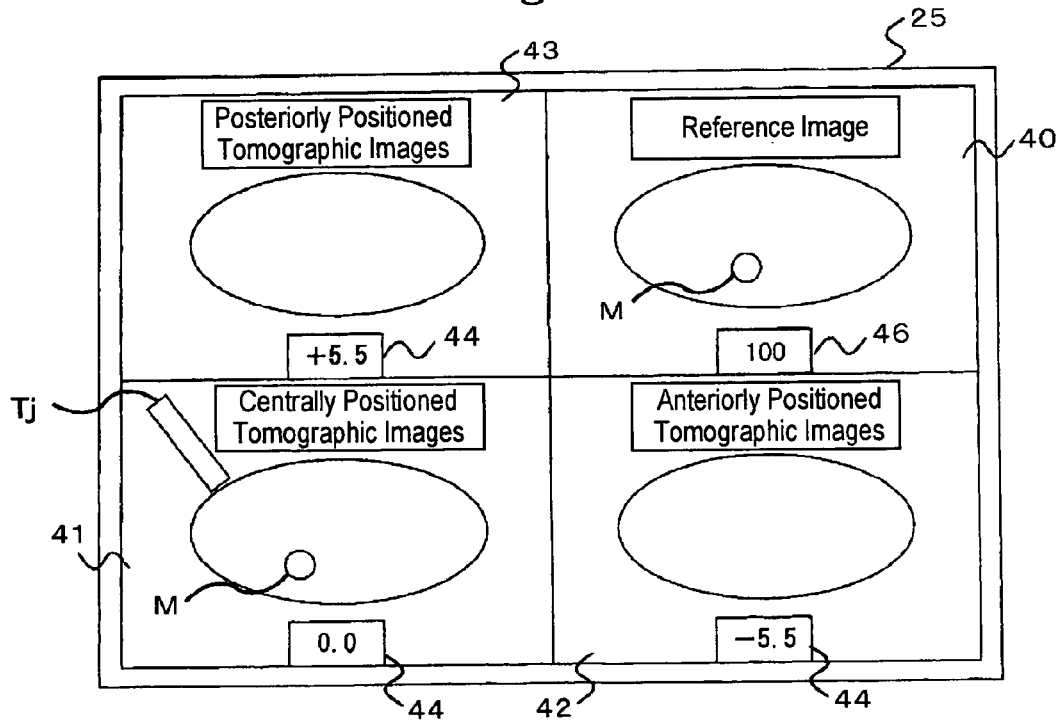

TOMOGRAPHIC SYSTEM

TECHNICAL FIELD

This disclosure relates to a tomographic system, and in particular to the tomographic system which is devised to assist the determination of the position from which a treatment device such as puncture needle is inserted into the body of the subject or patient (subject, etc.) for performing necessary treatment.

BACKGROUND ART

Among the X ray CT systems of the tomographic systems, the multi-slice X ray CT system, which can obtain plural tomographic images in the axial direction of the body of the subject, etc., is used in increasingly many cases in recent years. In order for making able to obtain tomographic images for each of the plural tomographic positions (slice positions) set in the axial direction of the body of the subject, etc. simultaneously the multi-slice tomographic system is equipped with a two-dimensional detector as a means for detecting X ray. The two dimensional detector consists of plural arrays of X ray detection element arrays in which X ray detection elements are arranged linearly, and can performs multi-slice X ray CT imaging by obtaining projection data with each of the plural X ray detecting element array as a unit or with a certain number of X ray detection element arrays as a unit.

Such tomographic systems are used in the examination of the subject or the treatment of the patient with the method known as CT fluoroscopy. The CT fluoroscopy is used in biopsy, where the tissue is taken for examination with a puncture needle from the tumor site in the subject, etc., by inserting a treatment device such as puncture needle into the intended treatment area (the primary tumor site in case of tumor biopsy of the subject, etc.,) and performing necessary procedures (such as obtaining the tissue for examination).

The technology associated with the conventional CT fluoroscopy is to assist the determination of the position from which treatment device is inserted by displaying the plural time-series tomographic images successively (See Patent Document 1).
Patent document 1: Japanese Patent Application Laid-Open No. 2000-287962

However, according to the afore-mentioned patent document 1, the position from which the treatment device is inserted should be determined before insertion of the device into the subject, etc. Therefore, the information required for determining the insert position may not be obtained only from the successive and time-series displayed images in some cases, in which the tomographic images must be taken in the trial and error process. Tt means that the needs for assisting the insertion of the treatment device, namely the needs for reducing the trouble of such trial and error process, cannot be served. Moreover, such needs include not only greater convenience for the operator who performs the treatment, such as improved throughput of diagnosis and examination, but also the advantages for the subjects, etc., who receive examination or treatment, such as reduced X ray exposure dose and shortened hours of treatment.

SUMMARY

In an aspect of this disclosure, there is provided a tomographic system, with which the position from which the treatment device is inserted for the subject can be determined efficiently.

The above-mentioned tomographic system can comprise a scanning means for simultaneously obtaining tomographic images at plural tomographic positions in the axial direction of a body of a subject, display means for displaying the plural tomographic images thus obtained, a relative distance between tomographic images computing means for computing relative distances at each tomographic position for the plural tomographic images, and a control means for controlling a display of the computed relative distance between tomographic images and the obtained plural tomographic images.

When the above-mentioned tomographic system is used, the operator can see the displayed data of the relative distances between tomographic images and the length of the treatment device instantaneously, and can therefore efficiently determine the insert position of the treatment device for the subject.

BRIEF EXPLANATION OF DRAWINGS

[FIG. 3] A diagram illustrating an example of display screen on the display device.

[FIG. 4] A diagram illustrating another example of display screen of the display device.

EXPLANATION OF SYMBOLS

Figure 1:
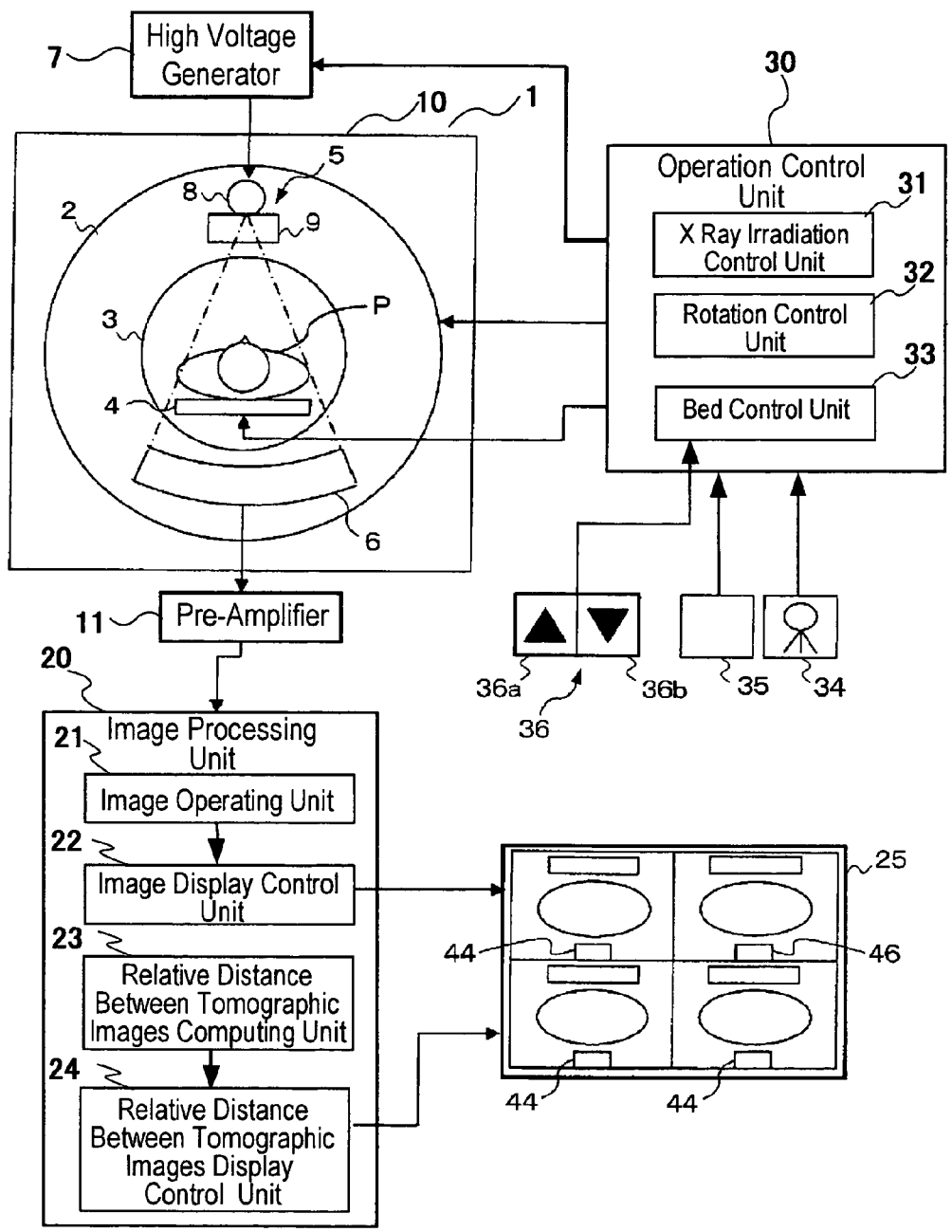
[FIG. 1] A block diagram illustrating the configuration of a tomographic system of an embodiment of the present invention.

10 Scanning unit
20 Image processing unit
23 Relative distance between tomographic images computing unit
25 Display unit
30 Operation control unit
34 Direction input means
40 Reference image
41 Centrally positioned tomographic image
42 Anteriorly positioned tomographic image
43 Posteriorly positioned tomographic image
44 Distance display frame
P Subject
T Puncture needle (procedure device)

PREFERRED EMBODIMENT OF THE INVENTION

Embodiments of the present invention are explained below. FIG. 1 is a block diagram illustrating the configuration of the tomographic system according to an embodiment of the present invention.

The tomographic system of this embodiment is mainly provided with the scanning unit 10, which obtains tomographic images of the subject P, the image processing unit 20, in which the projective data signals obtained in the scanning unit 10 are processed to produce and display images, and the operation control unit 30, which controls the scanning operation.

The scanning unit 10 is equipped with the gantry 1, which has the built-in annular rotating frame 2 devised to rotate clockwise or anti clockwise as shown in the figure. At the center of the rotation frame 2, there is the opening 3, through which the bed 4 carrying a lying subject can be moved back and forth. In the rotation frame 2, the X ray irradiating means 5 and the X ray detecting means 6 are installed as they are opposed with the opening 3 between them. The gantry 1 is equipped with a position indicating means (not illustrated) for indicating the scanning position (a slice position or a central slice position for multi slices), by visually marking the body surface of the subject P. The indication of the position is the position marking irradiated by laser light and is used as an index for the insert position when the puncture, etc. is performed.

The X ray irradiating means 5 is provided with the X ray source 8 of X ray tube type, which is activated by the high voltage to be supplied from the high voltage generator 7 and irradiates X ray, and the collimator 9, which controls the X ray irradiated from the X ray source 8 into a cone beam X ray at an appropriate angle.

The X ray detecting means 6 is provided with a two-dimensional detector of the structure, in which the plural X ray detection element arrays consisting of linearly aligned X ray detection elements are arranged. It is devised to ensure that the multi-slice X ray CT imaging is performed by obtaining projection data with each of these plural X ray detection element arrays as a unit or with a certain number of X ray detection element arrays as a unit. The projection data signals from the X ray detection means 6 are transmitted to the image processing unit 20, after amplification by the pre-amplifier 11.

The image processing unit 20 comprises the image operating unit 21, the image display control unit 22, the relative distance between tomographic images computing unit 23, and the relative distance between tomographic images display control unit 24. The image operating unit 21 reconstructs the tomographic images from projection data, and the tomographic images generated by the image operating unit 21 are displayed on the screen of the display device 25 under the control of the image display control unit 22. The image display control unit 22 has a function to display plural tomographic images obtained simultaneously in the multi-slice CT imaging in given order on the screen of the display device 25. The relative distance between tomographic images computing unit 23 computes the relative distances from one reference image for each tomographic images, while the relative distance between tomographic images display control unit 24 controls displaying of the computed relative distances on the display device 25.

The operation control unit 30 controls the operation of the scanning unit 10 in the obtaining of tomographic images for the patient P lying on the bed 4, by rotating the rotation frame 2 and adjusting the angle of X ray irradiation to a certain range for the subject P and moving the slice position by moving the bed 4 back and forth against the opening 3. The operation control unit 30 has the X ray irradiation control unit 31, the rotation control unit 32 and the bed control unit 33. As a means for inputting direction (instruction) into every control unit, for example, the foot switches 34-36 are connected. The foot switch is shown as an example direction input means, but other switches such as those which can input direction by using a part of the body, vocal input means and eye-movement input means are also available.

The X ray irradiation control unit 31 controls the X ray irradiation means 5 via the high-voltage generator 7. The X ray irradiation means 5 is controlled by the X ray irradiation control unit 31 with a shutter method. The control with the shutter method is to ensure that, in the puncture procedure to be discussed later, for example, the irradiation of X ray by the X ray irradiation means 5 is limited only to the time of rotation scanning over a certain angular range (for example 360 degree) of the rotation frame 2, according to the operator's direction to commence X ray irradiation by stepping the foot switch 34. This is disclosed in Patent Document 2.

Patent Document 2: Japanese Patent Application Laid-open No. 2004-180711

The rotation control unit 32 controls the rotation of the rotation frame 2. Specifically, when the operator steps the foot switch 35, namely the direction input means, to send direction, the direction is sent to the X ray irradiation control unit 31, the rotation control unit 32 and the bed control unit 33. Then the X ray is irradiated with the rotation frame 2 being rotated, and at the same time the bed 4 is moved and obtaining tomographic images commences. In the scannography, another direction input means (not illustrated), which is independently is installed, may be used.

The bed control unit 33 enables, as the X ray irradiation control unit 31 and the rotation control unit 32, the individual control of back and forth movement of the bed 4. The foot switch 36 for controlling the bed movement is provided with the forward movement foot switch 36a and the backward movement foot switch 36b, and the bed 4 moves forward or backward only while the operator steps the forward movement foot switch 36a or the backward movement foot switch 36b. The information concerning the bed position (coordinates) obtained by the operation of the foot switch 36 is provided from the position detector (not illustrated) or the bed control unit 33 to the image processing unit 20, and is displayed in association with the tomographic images.

The biopsy by using a puncture needle, for example, for a multi-slice tomographic system, is performed with the following procedures. Firstly, the subject undergoes scannography. The scannography is a fluoroscopic imaging performed to obtain projection images of the subject. The tomographic images are taken over the range including the intended biopsy area based on the scanographic images. Then, based on the tomographic images thus obtained for the intended biopsy area, a puncture plan is formulated. Then, after the scan for determining the puncture position, the puncture is performed while confirming the situation of the puncture needle (how the puncture needle is inserted) by using the tomographic images taken at the puncture position.

In the procedure of scan for determining the puncture position, firstly the intended puncture position is scanned as a trial, based on the tomographic images of the afore-mentioned intended biopsy area. Namely, the scan is performed on the slice positions with the intended puncture position as a center, based on the tomographic images for the afore-mentioned intended biopsy area. The plural tomographic images thus obtained are displayed in an appropriate order on the screen of the display device.

It is assumed here that tomographic images for 3 slices are displayed in the multi-slice X ray CT imaging. If the tomographic images for these 3 slices are centrally, anteriorly and posteriorly positioned images, the slice position of the centrally positioned tomographic image will be visually displayed on the body surface of the subject by the position indicating means such as irradiation of laser light. And the puncture needle will be inserted into the position thus displayed. In other words, the scan for determining the puncture position is performed in order to find the slice position, with which the intended biopsy area comes in view on the centrally positioned tomographic image.

Once the puncture position is determined, the puncture is performed after finely adjusting the position and the direction of the insertion of the puncture needle as required. The puncture is performed by checking the situation of the puncture needle through the display on the tomographic images taken with the puncture position being considered as a slice position of the centrally positioned tomographic images.

Main characteristics of the tomographic system of this embodiment are explained below in association with the examples of puncture biopsy operation performed by using the tomographic system.

Figure 2:
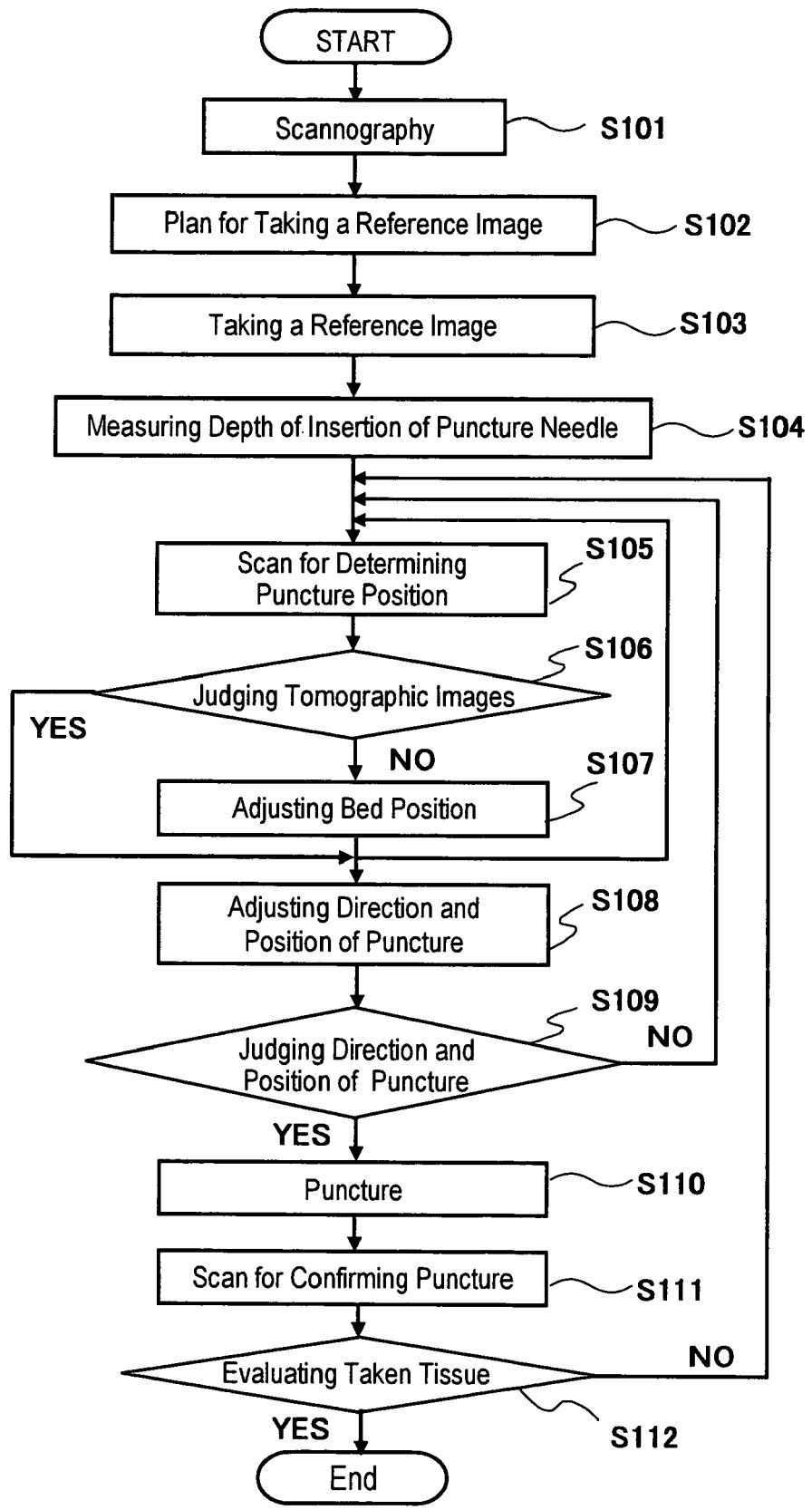
[FIG. 2] A flow chart showing an example of the process of the puncture biopsy.

FIG. 2 shows an example of the puncture biopsy procedures. Firstly, scannography is performed of the subject (Step 101). Scannography is performed by an operator to obtain projection images of the subject, and is performed as a radiographic fluoroscopy. Then, the plan for taking a reference image based on the scannographic images is formulated (Step 102), and the reference image is taken according to this plan (Step 103). The reference image covers the range including the intended biopsy area and is taken prior to the puncture. The reference image is used by the operator in planning the depth and the angle of the insertion of the puncture needle in advance. It is also used in determining the approximate slice positions for scanning to determine the puncture position.

In addition to the determination of slice positions, the reference image may be a three-dimensional image constructed by using tomographic images taken over the range including the intended biopsy area and may be used for three-dimensionally understanding the situation of the needle. Here, a technique or method known in the art (For example, Patent Document 3) can be used for constructing these three-dimensional images.

Patent document 3: Japanese Patent Publication No. 6-34238

In this embodiment the reference image is taken in the step 103. However, the reference image can also be the tomographic images taken 6 months to one year ago for the area which is approximately same as the range containing the intended biopsy area of the subject him/herself. In the latter case, the conditions can be compared with those in the past.

Further, the reference image includes the images that are used in formulating a treatment plan, such as tomographic images of other subject with similar symptoms to be treated, and the tomographic images of other subject who is in the similar generation and has similar age or similar body figure to the subject. In this case, a search key technology known in the art that allows to find desired tomographic images by inputting desired symptoms, age and body figure of the subject (for example, Patent Document 4) can be used. By the use of this search key, a desired tomographic image can be found and displayed as a reference image.

Patent document 4: Japanese Patent Application Laid-Open No. 2005-73818

In short, the reference image may be interpreted broadly to include any images that can assist the insertion of a treatment device into the body of the subject.

For displaying such reference image, the image display control unit 22 is devised, as shown in FIG. 3, to remain the display of the reference image 40 within the reference image display frame set on the screen of the display device 25 during the performance of the trial scan for determining the puncture position. It is further preferred that a position display frame 46 is provided on this reference image 40 and that the slice position data for the reference image 40 can be displayed on this position display frame 46. The slice position data of the reference image 40 can be obtained, for example, as coordinate values along the longitudinal axis of the bed 4. When the taking of the reference images is completed, the depth of insertion of the puncture needle is measured with this reference image (Step 104).

Then, the scanning unit 10 performs scanning for determining a puncture position (step 105). In the scanning for determining the puncture position, first of all, a trial scanning of a slice position, which has been roughly estimated as an intended puncture position with the reference image 40 displayed on the display device 25, is performed. This is a multi-slice X ray CT imaging, and in this embodiment of the invention the tomographic images for three slices, the tomographic image positioned centrally relative to the slice direction (centrally positioned tomographic images) 41, tomographic image positioned anteriorly relative to the slice direction (anteriorly position tomographic images) 42 and tomographic image positioned posteriorly relative to the slice direction (posteriorly position tomographic image) 43 are obtained. Every tomographic image is displayed in given order within the multi-slice image frame established in parallel with the reference image frame on the screen of the display device 25.

These three tomographic image display frames have the distance display frame 44 that displays the distance between the slices of each tomographic image. On this distance display frame 44, the distance of the anteriorly positioned tomographic image 42 or the posteriorly positioned tomographic image 43 from the reference (zero), which is defined as a position of the centrally positioned tomographic image 41, is displayed. The relative distance between tomographic images is determined by the thickness of the slice of each tomographic image, and the thickness of the slice of each tomographic image is determined by the number of X ray detection element arrays to be used for each tomographic image and computed by the relative distance between tomographic images computing unit 23.

Specifically, the tomographic image for one slice is reconstructed with the projection data from n lines (n=1, 2, 3 . . . ) of X ray detection element arrays, while the thickness of one slice for a tomographic image is n-fold of the width of X ray detection element array. Such slice thickness can be selectively set by the operator with the control panel (not illustrated) installed in the tomographic system shown in FIG. 1. The relative distance between tomographic images computing unit 23 computes the relative distance between tomographic images based on the slice thickness set by the operator.

The operator examines three displayed tomographic images and judges whether or not the intended biopsy area is contained (positioned) properly in the images (Step 106). When it is known that, at this slice position, the intended biopsy area is contained properly in the centrally positioned tomographic image 41 as shown in FIG. 4, the judgment result of the step 106 is affirmed (YES) and the determination of the puncture position is completed. Since the slice position of the subject corresponding to the centrally positioned tomographic image 41 is visually marked by the position indicating means such as laser irradiation (not illustrated), such position indication mark is used to indicate the puncture position.

When the judgment result for the Step 106 is negative (NO), namely the intended biopsy area is not contained in any of the tomographic images, or the intended biopsy area is contained in other tomographic images than the centrally positioned image, such as anteriorly positioned or posteriorly positioned tomographic images (in the example of FIG. 3, the tumor site M, the intended biopsy area, is in the anteriorly positioned tomographic image 42), the slice position should be changed and adjusted by moving the bed 4 (Step 107).

The slice position is changed by moving the bed 4 by operating the foot switch 36. With the movement of the bed 4, the figures corresponding to the distance of movement are displayed within the distance display frame of the centrally positioned tomographic image 41. These figures are calculated by the relative distance between tomographic images computing unit 23 based on the position information (coordinate values) of the bed 4 obtained from the bed 4 or the bed control unit 33, and displayed by the relative distance between tomographic distances display control unit 23 on the display device 25. In this case, the display of the figures is controlled to change hourly in accordance with the movement. The operator estimates appropriate distance of the movement by referring to the three tomographic images and the relative distances between tomographic images displayed on the screen, and then moves the bed 4 while referring to the figures corresponding to the distance of movement displayed on the distance display frame 44.

In the example shown in FIG. 3, the distance value of the slice position of the centrally positioned tomographic image 41, which is a reference value, the anteriorly positioned tomographic image 42 and the posteriorly positioned tomographic image 42 are 0.0 mm, −5.5, and +5.5 mm, respectively. Since the intended biopsy area is contained in the anteriorly positioned tomographic image 42, it is judged to be moved to the slice position where the anteriorly positioned tomographic image 42 becomes the centrally positioned tomographic image. The distance of movement in this case is +5.5 mm. When the movement of the bed 4 is commenced by operating the foot switch 36, the distance value in the distance display frame 44 of the centrally positioned tomographic image changes in real time as +1, +2 . . . +5, in accordance with the movement. At the same time, the distance values of the slice position of the anteriorly positioned tomographic image 42 and the posteriorly positioned tomographic image 43 change from −5.5 to 0, and +5.5 to 11 respectively. And when the distance value of the slice position of the centrally positioned tomographic image 41 becomes +5.5 mm, the movement of the bed 4 is suspended, and the tomographic image is taken by operating the foot switch 34 and irradiating X ray with a shutter method. By this, the tomographic images for 3 slices in which the slice position of the anterior positioned tomographic image 42 becomes a new centrally positioned tomographic image are obtained.

As mentioned above, the relative distances between plural tomographic images obtained by scanning at plural tomographic positions are computed by the relative distance between tomographic images computing unit and displayed with corresponding plural tomographic images by the relative distance between tomographic images display control unit, so that it is possible to refer to the display of this relative distance between tomographic images.

In the case where the intended biopsy area is seen in two of the three tomographic images, it is possible to estimate to which tomographic image the intended biopsy area is closer among the two tomographic images, from the presence of the intended biopsy area, and therefore to estimate the distance to move the bed 4 based on the information obtained from the images and the relative distances displayed as superimposed on the images.

Also even in the case where the tumor site M is not seen in any of the tomographic images 41, 42 or 43, it is possible to estimate an appropriate intended puncture position by referring to the relative distances displayed. In this case, it is further easier to estimate the intended puncture position by referring to the reference screen 40 and the display of its slice position data, in addition to the display of relative distances.

When three tomographic images taken in a new slice position are obtained, three previous tomographic images displayed on the display screen are updated to the new centrally, anteriorly and posteriorly positioned tomographic images taken in a new slice position. At the same time, the distance values displayed in the distance display frame of the centrally positioned tomographic image 41 are also reset and returned to zero. Consequently, only the distance value for the centrally positioned tomographic image 41 needs to be changed in real time, and the data processing work load of the relative distance between tomographic images computing unit 23 and the relative distance between tomographic images display control unit 24 can be reduced dramatically.

In this embodiment of the present invention, since the reference image 40 is displayed in parallel on the display screen and the scanning of step 105 can be performed while referring to the reference image, it is highly possible that the intended biopsy area is contained in either of the these three tomographic images in the first scan. Accordingly, in almost all cases, the afore-mentioned scan for determining the position can be completed by only one or two times of scanning. If necessary, the adjustment of the bed position (step 107) and the scan for determining the position (step 106) are re-performed by referring to the display of new three tomographic images and their relative distances.

Once the puncture position is thus determined, the direction and the position of puncture are adjusted finally by referring to the tomographic images taken at that position (Step 108). FIG. 4 shows the examples which display the tomographic images 41, 42 and 43 taken at the slice position with which the tumor site M comes in view in the centrally positioned tomographic image 41. Adjusting a fixing jig Tj that retains a puncture needle by referring to such visual display on the screen, the direction and the position of puncture are finally adjusted.

Once the final adjustment of the direction and the position of puncture is completed, operator judges their appropriateness of the resulted direction and position of puncture (Step 109). When they are judged appropriate (YES) and the direction and the position of puncture are confirmed, the puncture is commenced (Step 110). When the direction and the position of puncture are judged inappropriate (NO), the operator returns to the step 105 and re-performs the procedures from the step 105 to the step 108.

The puncture can be performed while serially scanning at the puncture position and by watching the situation of the puncture needle on the time-series tomographic images obtained. Namely, since the puncture needle T comes in view on the centrally positioned tomographic image 41 in the tomographic images taken with the puncture position as a slice position, as illustrated in FIG. 5, the puncture is performed by watching the situation of the puncture needle T displayed on the tomographic images.

Figure 5:
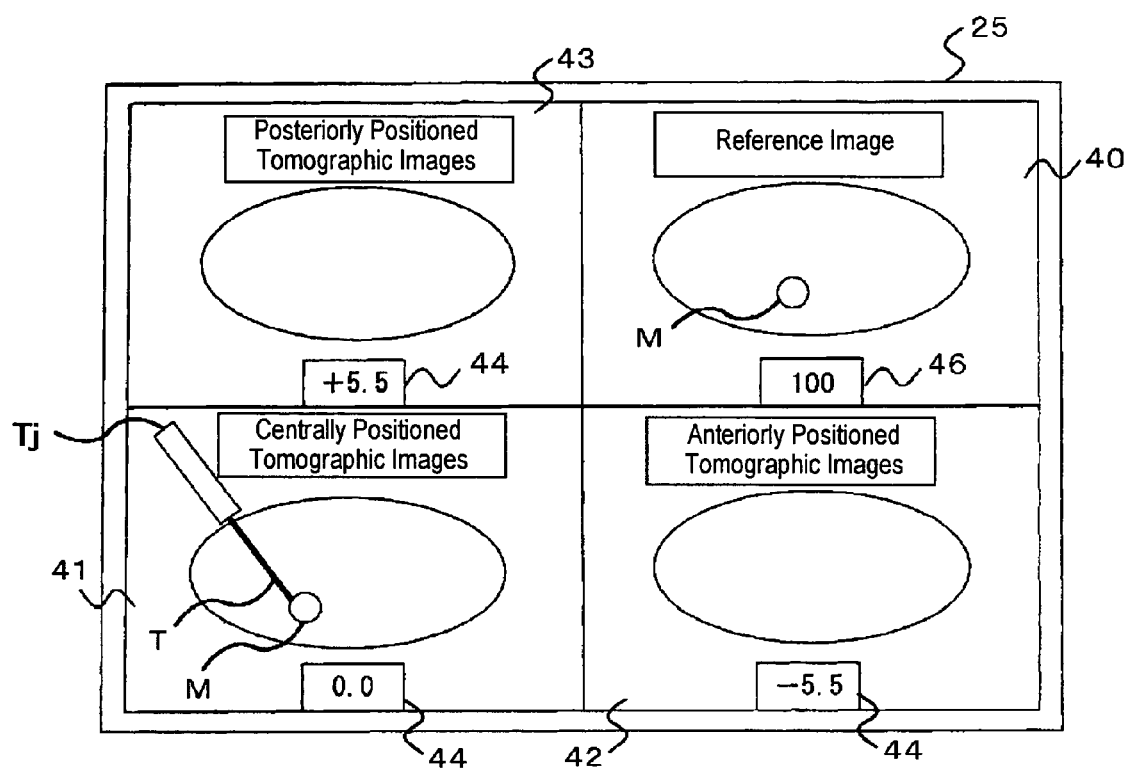
[FIG. 5] A diagram illustrating further another example of display screen of the display device.

In the biopsy puncture, the puncture needle T is inserted into the tumor site M to take a portion of the tissue from the site (the conditions shown in FIG. 5). In this puncture procedure, a confirming scan is performed for the purpose of confirming later how the puncture needle T is inserted into the tumor site M (Step 111). The quantity and the condition of the tissue taken by the puncture are examined whether or not the tissue taken is adequate both quantitatively and qualitatively (Step 112). If it is confirmed adequate (YES), the procedure is completed, whereas if it is confirmed inadequate (NO), the operator returns to the step 105 and re-perform the step 105 to the step 111.

The tissue is usually taken from at least two positions of the tumor site M. In this case, if the tumor site M is large, the positions from which the tissue is taken may be far apart, so that the step 5 is performed every time the tissue is taken from two or more positions.

Embodiments of the present invention are explained above with the puncture biopsy procedures as an example. According to the embodiment of the present invention, the following effects are obtained.

1) In the scan to determine the puncture position, the operator can numerically grasp the distance which the bed 4 needs to be moved from the display of relative distances between tomographic images and know the approximate distance to move the bed 4 based on it. Therefore, in comparison with the conventional methods which rely entirely upon the operator's intuition alone, the number of trial scanning until the tumor site 41 comes in view in the centrally positioned tomographic image 41 can be reduced dramatically.

2) The reduced number of trial scanning improves the efficiency of the puncture biopsy procedure and minimizes the increase in the quantity of X ray exposure by multi-slice CT.

3) Since the trial scanning can be performed by referring to the reference image 40 displayed in parallel on the display device 25, the possibility that the tumor site 41 comes into view in either of the tomographic images at the first trial scanning is high. And if the tumor site M comes into view in the centrally positioned tomographic image 41 at the first trial scanning, the scan for determining the position can be completed with only one trial.

In this case, the number of trial scan for determining the puncture position can be reduced to a half or less of the conventional average three times, and therefore, the irradiation time required for determining the puncture position can be reduced to a half or less. For a large tumor site which requires more than two punctures, this is particularly effective.

The above-mentioned embodiments explain the cases of X ray irradiation control with a shutter method, and the embodiment of this invention can be applied to the case in which X ray is continuously irradiated while moving the bed. In this case, the benefit of the display of relative distances and the real time changes of the distance value is further higher. More specifically, when the continuous X ray irradiation is used in the scan for determining the puncture position, the conventional methods cause differences in the bed 4 position between the slice position at the time when the tomographic image is take and the slice position at the time when the tomographic image is displayed, and requires long time for the scan for determining the puncture position. In this embodiment, however, it is possible to change the distance value for the centrally positioned tomographic image in real time in accordance with the movement of the bed 4, and when the value reaches a given point the X ray irradiation can be suspended. Therefore, the generation of difference in positions is prevented, and the puncture position is determined efficiently and quickly.

Since the scan for determining the puncture position can be completed in 5 seconds or less in average by using the display of the relative distances between tomographic images, the length of X ray irradiation time can be reduced to ⅓ or less of the conventional scanning procedure which required 15 seconds or more in average.

According to this embodiment, the puncture position can be determined efficiently and the length of X ray irradiation time is reduced dramatically, and therefore the X ray exposure to the subject or operator before the final determination of the puncture position can be reduced. Such favorable effects of this embodiment are efficiently exerted in the X ray irradiation with both shutter and continuous methods. But the dose of X ray exposure is further reduced when the shutter method is used, because of the X ray exposure reducing effect the shutter method itself has.

According to the tomographic system of this embodiment, the control means is equipped with the direction input means for controlling X ray irradiation, and can control the commencement and the suspension (start and stop) of X ray irradiation to the afore-mentioned subject by operating the direction input means.

The tomographic system of this embodiment comprises a scanning means having an X ray source and an X ray detector, which are placed as opposed with the subject therebetween and are driven to rotate around the subject and a moving means to move the subject, an operation control means to control the operation of the scanning means, an image processing means for processing the signals detected by the X ray detector of the scanning means so as to generate tomographic image of the subject, and a display means for displaying the tomographic images produced by the image processing means. The image processing means displays plural tomographic images obtained simultaneously by the scanning means in parallel and also displays the position information (relative distance) of other tomographic images with the tomographic position corresponding to one of the plural tomographic images as a reference, together with the plural tomographic images on the display means.

Since the position information of other tomographic images are thus displayed together with the plural tomographic images, the displayed information which is used to improve the efficiency to determine the position in the CT fluoroscopy can be provided.

In this embodiment, preferably, the displayed values of relative distances between tomographic images change according to the operation for moving the tomographic position of the subject by the moving means which move the subject in the axial direction of the body of the subject.

This enables the operator who performs CT fluoroscopy to know the up to date scanning position in real time, thereby contributing to the further improving the efficiency of the CT fluoroscopy.

Also in this embodiment, preferably, the tomographic image taken in advance for the intended treatment area of the subject are defined as a reference image, and this reference image is displayed in parallel with plural tomographic images displayed on the display means.

Since this allows for the operator who performs CT fluoroscopy to compare the tomographic images with the reference tomographic image, which is obtained in advance by taking a tomographic image for the area including the intended biopsy area and displayed as a tomographic image without puncture, the planning for the insertion of a puncture needle using the reference image can be formulated more easily, thereby contributing to the further improvement in the efficiency of the CT fluoroscopic procedure.

Moreover, this embodiment can be applied not only to the X ray tomographic system but also to any equipment or system in which tomographic images are taken at plural tomographic positions perpendicular to the direction of moving the subject, and such tomographic images are used to assist the insertion of the treatment device. In such applications, the time required for determining the position of insertion can be reduced dramatically. For example, this embodiment can be applied to the tomographic systems for taking tomographic images of a subject, including MRI system and PET system.

The MRI system, for example, comprises a magnetostatic magnet which generates a homogeneous magnetostatic field in the space where a subject is placed, a gradient magnetic field coil that forms magnetic gradient in this space, an irradiation coil that irradiates to the nucleus of the atoms constituting the tissue of the subject with a high frequency magnetic field, whose frequency is the same as the resonance frequency of the nucleus, a receiving coil which receives NMR signals generated from the subject, an image processing means which processes the NMR signals received by this receiving coil and computes so as to reconstruct the tomographic images of the subjects, and displays the tomographic images of the aforementioned subject which are reconstructed by the image processing means.

The magnetostatic magnet, the gradient magnetic field coil, the irradiation coil, and the receiving coil constitute a scanning means in the MRI system.

Since the MRI system can obtain plural tomographic images along the axial direction of the body of the subject, the technology employed in the X ray CT system can be applied also to the biopsy using MRI images.

Namely, the image processing means displays in parallel with the plural tomographic images taken simultaneously by using the scanning means and the position information for other tomographic images with the tomographic position corresponding to one of the afore-mentioned plural tomographic images as a reference (relative distance), together with the plural tomographic images on the display means.

Since the position information for other tomographic images are thus displayed with the plural tomographic images, the displayed information for improving the efficiency to determine the position of insertion in biopsy with MRI images can be provided.

In this embodiment, preferably, the displayed relative distances between tomographic images change in real time according to the movement of the tomographic position of the subject by using a moving means to move the subject in the axial direction of the body of the subject.

This allows the operator who performs biopsy with MRI images to know the up to date scanning position in real time, thereby contributing to the further improvement of the efficiency of biopsy with MRI images.

Also in this embodiment, preferably, a tomographic image taken in advance for the intended treatment area of the subject is defined as a reference image, and this reference image is displayed in parallel with plural tomographic images displayed on the display means.

Since this allows for the operator who performs biopsy with MRI images to compare tomographic images with the reference tomographic image, which is obtained in advance by taking tomographic images for the area including the intended biopsy area and displayed as a tomographic image without puncture, the planning for the insertion of a puncture needle using the reference image can be formulated more easily, thereby contributing to the further improvement of the efficiency of the biopsy with the MRI system.

The invention claimed is:

1. A tomographic system comprising:
a scanning unit that simultaneously obtains plural tomographic images at respective tomographic positions in an axial direction of a body of a subject;
a display unit that displays the plural tomographic images thus obtained;
a relative distance computing part that computes, for each of the plural tomographic images, a slice distance between a slice position of the tomographic image and a slice position of a centrally positioned tomographic image amongst the plural tomographic images; and
a control unit that controls a display of the computed slice distances between the respective tomographic images and the centrally positioned tomographic image,
wherein at least one of the plural tomographic images is anteriorly positioned, in the axial direction, relative to the centrally positioned tomographic image, and at least one of the plural tomographic images is posteriorly positioned, in the axial direction, relative to the centrally positioned tomographic image, and
the display unit simultaneously displays the anteriorly positioned tomographic image, the posteriorly positioned tomographic image, and the centrally positioned tomographic image, along with the computed slice distances of the anteriorly positioned image and the posteriorly positioned image, respectively, to the centrally positioned tomographic image.

2. The tomographic system according to claim 1, wherein the relative distance computing unit computes a distance and a sign relative to a position of a reference tomographic image for the plural tomographic images.

3. The tomographic system according to claim 1, wherein the control unit causes the display unit to display at least three of the plural tomographic images in arbitrary order and to display the relative distances between tomographic images corresponding to each of the plural tomographic images displayed in arbitrary order.

4. The tomographic system according to claim 1, wherein a moving unit that moves the subject in the axial direction of the body, and
the control unit causes display of displayed values of the relative distances between tomographic images to change in real time according to the operation for changing the tomographic position of the subject by the moving unit.

5. The tomographic system according to claim 4, wherein the control unit resets displayed values of the relative distances between tomographic images to an initial value after the movement by the moving unit.

6. The tomographic system according to claim 4, wherein the display unit is used for confirming a position from which a treatment device is inserted into the body of the subject on the plural tomographic images, and
the moving unit moves the subject in the axial direction of the body in accordance with the movement of the position from which the treatment device is inserted.

7. The tomographic system according to claim 1, wherein the control unit displays a reference image for assisting insertion of the treatment device into the body of the subject in parallel with the plural tomographic images displayed on the screen of the display unit.

8. The tomographic system according to claim 7, wherein the control unit displays a tomographic image that has been taken in advance for an intended treatment area in the a subject, as the reference image.

9. The tomographic system according to claim 7, wherein the control unit displays a three-dimensional image constructed from tomographic images that have been taken in advance for an intended treatment area in the subject, as the reference image.

10. The tomographic system according to claim 7, wherein the control unit displays a tomographic image of other subject who has similar symptoms to those shown in an intended treatment area of the subject, as the reference image.

11. The tomographic system according to claim 7, wherein the control unit displays a tomographic image of other subject who is in the similar generation and has similar age or body figure to the subject, as the reference image.

12. The tomographic system according to claim 1, wherein the control unit comprises a direction input unit for controlling X ray irradiation, and the control unit controls a commencement and a suspension of X ray irradiation for the subject through operating the direction input unit.

13. A tomographic system comprising:
a scanning unit having an X ray source and an X ray detector, which are placed as opposed with a subject therebetween and are driven to rotate around the subject, and a moving means to move the subject,
an operation control unit to control an operation of the scanning unit,
an image processing unit for processing signals detected by the X ray detector of the scanning unit so as to generate a tomographic image of the subject, and
a display unit for displaying the tomographic image produced by the image processing unit, wherein
the image processing unit causes the display unit to display plural tomographic images obtained simultaneously by the scanning unit in parallel and additionally display, along with the plural tomographic images, position information representing slice distances between slice positions of the plural tomographic images, respectively, to a slice position corresponding to one of the plural tomographic images as a reference image, together with the plural tomographic images on the display unit,
wherein at least one of the plural tomographic images is anteriorly positioned, in an axial direction of a body of the subject, relative to the reference image, and at least one of the plural tomographic images is posteriorly positioned, in the axial direction, relative to the reference image, and
the display unit simultaneously displays the anteriorly positioned tomographic image, the posteriorly positioned tomographic image, and the reference image, along with the computed slice distances of the anteriorly positioned image and the posteriorly positioned image, respectively, to the reference image.

14. The tomographic system according to claim 13, wherein
the image processing unit inputs information on the changes in the tomographic position produced by operation of the moving means, and updates and displays in real time on the display unit the changes in the tomographic position of the reference associated with the movement by the moving means.

15. The tomographic system according to claim 13, wherein
the image processing unit uses a tomographic image that has been taken in advance for an intended treatment area of the subject as a reference image and displays the reference image in parallel with the plural tomographic images on a screen of the display unit.

16. A tomographic system comprising
a scanning unit including
a magnetostatic magnet which generates a homogeneous static magnetic field in a space where a subject is placed, a gradient magnetic field coil which forms magnetic gradient in the space,
an irradiation coil which irradiates to nuclei of atoms constituting a tissue of the subject with high frequency magnetic field whose frequency is same as a resonance frequency of the nuclei, and
a receiving coil which receives NMR signals generated from the subject;
an image processing unit which processes the NMR signals received by the receiving coil and computes so as to reconstruct a tomographic image of the subject; and
an image display unit which displays the tomographic image reconstructed by the image processing unit, wherein
the image processing unit causes the image display unit to display plural tomographic images which are taken simultaneously in the scanning unit in parallel, and to display, along with the plural tomographic images, slice distances of slice positions of the plural tomographic images, respectively, to a slice position corresponding to one of the plural tomographic images as a reference image,
wherein at least one of the plural tomographic images is anteriorly positioned, in an axial direction of a body of the subject, relative to the reference image, and at least one of the plural tomographic images is posteriorly positioned, in the axial direction, relative to the reference image, and
the image display unit simultaneously displays the anteriorly positioned tomographic image, the posteriorly positioned tomographic image, and the reference image, along with the computed slice distances of the anteriorly positioned image and the posteriorly positioned image, respectively, to the reference image.

17. The tomographic system according to claim 16, wherein
the scanning unit further comprises a moving means for moving the subject, and
the image processing unit inputs information on the changes in the tomographic position produced by operation of the moving means, and updates and displays in real time on the image display unit the changes in the tomographic position of the reference associated with a movement by the moving means.

18. The tomographic system according to claim 16, wherein
the image processing unit uses a tomographic image that has been taken in advance for an intended treatment area for the subject as a reference image and displays the reference image in parallel with the plural tomographic images on a screen of the image displaying unit.

19. The tomographic scanning system according to claim 1, wherein
the control unit causes the display unit to display simultaneously images positioned at center, anterior and posterior in a scan direction among the plural tomographic images for judgment of whether an object inside the subject is included in the images.

20. The tomographic scanning system according to claim 4, wherein
the control unit causes the display unit to display simultaneously images positioned at center, anterior and posterior in a scan direction among the plural tomographic images together with the relative distance for each image for judgment of a moving distance of the moving means.

* * * * *